(12) United States Patent
Johnson et al.

(10) Patent No.: US 10,197,490 B2
(45) Date of Patent: Feb. 5, 2019

(54) APPARATUS, METHOD, AND SYSTEM FOR MEASURING RELATIVE PERMEABILITY OF IMMISCIBLE FLUIDS

(71) Applicant: DCI Corporation, North Salt Lake, UT (US)

(72) Inventors: Christopher F. Johnson, Bountiful, UT (US); Christopher Scott Johnson, Woods Cross, UT (US); Andrew C. Johnson, North Salt Lake, UT (US); Steven W. Derr, Salt Lake City, UT (US)

(73) Assignee: DCI CORPORATION, North Salt Lake, UT (US)

( * ) Notice: Subject to any disclaimer, the term of this patent is extended or adjusted under 35 U.S.C. 154(b) by 199 days.

(21) Appl. No.: 15/156,006

(22) Filed: May 16, 2016

(65) Prior Publication Data

US 2016/0356694 A1   Dec. 8, 2016

Related U.S. Application Data (60) Provisional application No. 62/169,908, filed on Jun. 2, 2015.

(51) Int. Cl.
| | | |
|---|---|---|
| *G01N 15/08* | (2006.01) | |
| *G01N 33/24* | (2006.01) | |
| *G01F 22/00* | (2006.01) | |
| *G01F 5/00* | (2006.01) | |

(52) U.S. Cl.
CPC ......... *G01N 15/0826* (2013.01); *G01N 33/24* (2013.01); *G01F 5/00* (2013.01); *G01F 22/00* (2013.01)

(58) Field of Classification Search
CPC .................................................. G01N 15/0826
See application file for complete search history.

(56) References Cited

U.S. PATENT DOCUMENTS

| | | | | | |
|---|---|---|---|---|---|
| 2,293,488 | A | * | 8/1942 | Bays ................... | G01N 15/0826 73/38 |
| 2,437,935 | A | * | 3/1948 | Brunner ................. | G01N 15/08 250/304 |
| 2,537,668 | A | * | 1/1951 | Hebard .............. | G01N 15/0886 73/38 |
| 4,506,542 | A | * | 3/1985 | Rose ................... | G01N 15/0826 73/38 |
| 5,263,360 | A | * | 11/1993 | Blauch ..................... | C09K 8/58 166/250.02 |

(Continued)

*Primary Examiner* — John Fitzgerald
(74) *Attorney, Agent, or Firm* — Kunzler, PC (57) ABSTRACT

An apparatus for measuring volumes of two or more immiscible fluids, a lighter fluid and a heavier fluid, in a core sample includes a fluid separator and two volume pressure actuators. The lighter fluid accumulates in an upper portion of the fluid separator and the heavier fluid accumulates in a lower portion of the fluid separator, with a meniscus forming between the lighter fluid and the heavier fluid. The first and second volume pressure actuators have fluid volume encoders that determine a net volumetric flow of the fluids to and from the fluid separator. The first and second volume pressure actuators also collectively maintain constant back pressure on the fluid separator and maintain the meniscus between the two immiscible fluids in the fluid separator at a constant position.

20 Claims, 7 Drawing Sheets

(56) References Cited

U.S. PATENT DOCUMENTS

| | | | | |
|---|---|---|---|---|
| 5,311,766 A | * | 5/1994 | Persoff | G01N 15/0826 73/38 |
| 5,503,001 A | * | 4/1996 | Wong | G01N 33/241 324/351 |
| 5,679,885 A | * | 10/1997 | Lenormand | G01N 15/0826 73/152.06 |
| 5,698,772 A | * | 12/1997 | Deruyter | G01N 15/0806 73/152.07 |
| 9,835,762 B2 | * | 12/2017 | Pairoys | G01V 9/00 |
| 2015/0219789 A1 | * | 8/2015 | Pairoys | G01V 9/00 73/118.04 |

* cited by examiner

APPARATUS, METHOD, AND SYSTEM FOR MEASURING RELATIVE PERMEABILITY OF IMMISCIBLE FLUIDS

CROSS-REFERENCE TO RELATED APPLICATION

This application claims the benefit of U.S. Provisional Patent Application No. 62/169,908 filed Jun. 2, 2015, which is incorporated herein by reference.

FIELD

This disclosure relates to fluid volume measurement, and more particularly relates to measuring the relative permeability of two immiscible fluids through a core sample.

BACKGROUND

Core analysts concerned with determining the nature of rock and fluid contained underneath the ground will often extract a core from, for example, an oil well and create core samples. The analysts will then conduct tests on the core samples to determine the core's characteristics.

One important characteristic of a core sample is relative permeability. Relative permeability relates to the flow characteristics of one fluid relative to a second fluid contained in the core sample. An important parameter in determining relative permeability is the saturation state of the sample—that is, the percentage of space (pore volume) in the sample that contains a first fluid, such as brine, and the percentage of that volume that contains a second fluid, such as oil. The measurement of relative permeability is often plotted as a function of sample saturation state.

Determining relative permeability is often done by the steady state method. This method involves choosing various fluid percentages to flow through the core sample until the fluid flow reaches steady state. For example, the core sample can be 100% brine saturated and a user can flow 100% oil into the core sample. Since the core sample is initially 100% brine saturated, initially the effluent from the core sample will also be 100% brine. However, the effluent will eventually include oil as the oil flows through the core sample, resulting in an effluent that is part oil and part brine. Once the oil flowing into the sample pushes all the brine that is able to be pushed out of the sample, the effluent will be 100% oil, resulting in a steady state or equilibrium, condition. In other words, steady state is achieved when flow of fluid into the core sample (100% oil) is the same as flow of fluid out of the core sample (also 100% oil).

The sample is now partially saturated with oil and partially saturated with brine (e.g., all the brine that is able to be flushed from the core sample has already been pushed out). The user determines the amount of brine remaining in the sample by measuring the volumes of oil and brine that have been flowed into the sample and the volumes that have gone out, and thereby determines the relative percentages of oil and brine remaining in the sample (i.e., the sample's saturation state).

In this sample case, the user then flows a different percentage of oil and brine into the core sample—say, 70% oil and 30% brine—until the system reaches a steady state or equilibrium, i.e., effluent that is also 70% oil and 30% brine. By determining the fluid volumes in and fluid volumes out, the user can then determine the core sample saturation state under those conditions, which will likely be different than when flowing 100% oil. The user then flows another percentage of oil and brine—say, 30% oil and 70% brine—until equilibrium is reached, similarly determining the sample saturation state under those conditions. The final percentage of fluid flow in may be 100% brine, with the sample saturation state determined using the same method.

In each of these cases, a large volume of fluid may need to be flowed through the core sample before equilibrium or steady state is achieved. If this large volume exceeds the finite volume of the traditional two-phase separator or similar system, the relative volumes of the two fluids can no longer be measured and the calculation will fail. Traditional two-phase separators also have the limitation of only being able to measure the change in volume of one of the two effluent fluids. This limitation makes it difficult to track the effluent flow rate of the second phase and accurately determine when steady state has been reached and the saturation state of the core sample. Therefore, there exists a need for an apparatus, method, and/or system that can accommodate and measure large volumes of fluid in order to determine sample saturation state.

SUMMARY

From the foregoing discussion, it should be apparent that a need exists for an apparatus, system, and method for measuring volumes of two or more immiscible fluids. Beneficially, such an apparatus, system, and method would allow users to continuously flow fluid through core sample under reservoir conditions to determine the relative permeability of immiscible fluids in a core sample and to determine the saturation state of the core sample.

The subject matter of the present application has been developed in response to the present state of the art, and in particular, in response to the problems and needs in the art that have not yet been fully solved by currently available systems. Accordingly, the present disclosure has been developed to provide an apparatus, system, and method for continuous flow of immiscible fluids through a core sample that overcomes many or all of the above-discussed shortcomings in the art.

Disclosed herein is one embodiment of an apparatus for measuring volumes of two or more immiscible fluids, at least a lighter fluid and a heavier fluid, in a core sample. The apparatus includes a fluid separator configured to gravity separate the two immiscible fluids. The fluid separator has an inlet, an upper portion, an upper portion outlet, a lower portion, and a lower portion outlet. The lighter fluid is configured to accumulate in the upper portion of the fluid separator and the heavier fluid is configured to accumulate in the lower portion of the fluid separator, with a meniscus forming between the lighter fluid and the heavier fluid. The apparatus also includes a first volume pressure actuator fluidly connected to the upper portion outlet of the upper portion of the fluid separator. The first volume pressure actuator has a first fluid volume encoder that determines a net volumetric flow of the lighter fluid from the upper portion of the fluid separator. The apparatus further includes a second volume pressure actuator fluidly connected to the lower portion outlet of the lower portion of the fluid separator. The second volume pressure actuator has a second fluid volume encoder that determines a net volumetric flow of the heavier fluid from the lower portion of the fluid separator. The first and second volume pressure actuators are responsible for collectively maintaining constant back pressure on the fluid separator and maintaining the meniscus between the two immiscible fluids in the fluid separator at a constant position.

In one implementation, the fluid separator has two chambers. The respective upper portions of the two chambers are fluidly interconnected via an upper connector and the respective lower portions of the two chambers are fluidly interconnected via a lower connector. In another implementation, each of the first and second volume pressure actuators is a pulseless syringe pump unit. For example, each pulseless syringe pump unit may include two syringe pumps that alternate active fluid communication with the fluid separator.

In another implementation, the apparatus further includes a meniscus position detector. For example, the meniscus position detector may be an acoustic transducer configuration or the meniscus position detector may be an optical sensor. In one implementation, the fluid separator is a first fluid separator and the apparatus further has a second fluid separator and a third volume pressure actuator. In other words, the apparatus may be configured to determine relative permeability of three immiscible fluids through the core sample. In yet another implementation, the apparatus is configured to determine relative permeability of "n" number of immiscible fluids, wherein the apparatus comprises "n" number of volume pressure actuators.

According to one implementation, the first volume pressure actuator maintains the constant back pressure on the fluid separator. In another implementation, the second volume pressure actuator is configured to maintain the meniscus between the two immiscible fluids in the fluid separator at a constant position.

Also disclosed herein is another embodiment of an apparatus for measuring volumes of two or more immiscible fluids, at least a lighter fluid and a heavier fluid, in a core sample. The apparatus includes a fluid separator configured to gravity separate the two immiscible fluids. The fluid separator has a first and a second chamber, with the first chamber having an inlet. Each chamber has an upper portion and a lower portion and the upper portion of the chambers are fluidly interconnected via an upper fluid connection passage and the lower portion of the chambers are fluid interconnected via a lower fluid connection passage. The lighter fluid is configured to accumulate in the upper portion of the chambers and the heavier fluid is configured to accumulate in the lower portion of the chambers, with a meniscus forming between the lighter fluid and the heavier fluid in the chambers. The interconnected upper portion of the chambers has an upper portion outlet and the lower portion of the chambers comprises a lower portion outlet.

The apparatus also includes a first volume pressure actuator fluidly connected to the upper portion outlet and a second volume pressure actuator fluid connected to the lower portion outlet. The first volume pressure actuator has two syringe pumps that each have first fluid volume encoders configured to determine a net volumetric flow of the lighter fluid to and from the upper portion of the chambers of the fluid separator. The second volume pressure actuator has two syringe pumps that each have second fluid volume encoders configured to determine a net volumetric flow of the heavier fluid to and from the lower portion of the chambers of the fluid separator. The apparatus also includes a meniscus position detector. The first and second volume pressure actuators collectively maintain constant back pressure on the fluid separator and maintain the meniscus between the two immiscible fluids in the fluid separator at a constant position.

Also disclosed herein is one embodiment of a method for measuring volumes of two or more immiscible fluids, at least a lighter fluid and a heavier fluid, in a core sample. The method includes pumping at least one of the lighter fluid and the heavier fluid through the core sample. The method also includes flowing a fluid effluent from the core sample into a fluid separator, with the lighter fluid accumulating in an upper portion of the fluid separator and the heavier fluid accumulating in a lower portion of the fluid separator. A meniscus forms between the lighter fluid and the heavier fluid. The method further includes determining net volumetric flow of the lighter fluid from the upper portion of the fluid separator via a first volume pressure actuator that is fluidly connected downstream of the upper portion of the fluid separator. Still further, the method includes determining net volumetric flow of the heavier fluid from the lower portion of the fluid separator via a second volume pressure actuator that is fluidly connected downstream of the lower portion of the fluid separator. The method also includes maintaining constant back pressure on the fluid separator and maintaining the meniscus at a constant position in the fluid separator via the first and second volume pressure actuators.

In one implementation, inlet flow of fluid through the core sample consists of the at least one of the lighter fluid and the heavier fluid and outlet flow of fluid from the core sample consists of the fluid effluent. In another implementation, at least one of the lighter fluid and the heavier fluid is continuously pumped through the core sample until a steady state condition is achieved. In yet another implementation, all of the method steps are performed under temperature and pressure conditions that are representative of the core from which the core sample was extracted. For example, the pressure condition under which the method steps are performed is at 5,000 psi.

In one implementation, the fluid separator has two chambers. The respective upper portions of the two chambers are fluidly interconnected via an upper connector and the respective lower portions of the two chambers are fluidly interconnected via a lower connector. In another implementation, each of the first and second volume pressure actuators is a pulseless syringe pump unit. For example, each pulseless syringe pump unit has two syringe pumps.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure.

As outlined above in the Background section, one method of determining sample saturation state is by material balance. The user begins with a known saturation state of the core sample (for example, 100% brine saturated). He then causes fluids to flow into the sample—e.g., oil and brine, generally under high pressure—and then calculates the current saturation state by comparing the volume of the fluids that have went into the core sample with the volume of the fluids that have flowed out of the core sample. The individual volumes flowed into the sample are easily known, as typically separate pumps are used to flow the separate fluids into the sample. However, the effluent from the core sample contains a combination of fluids, and the volume of each of the fluids must be determined accurately in order to be able to correctly calculate the volume of each fluid remaining in the core sample.

Moreover, it is preferable for accuracy that the relative permeability measurements be conducted at "reservoir conditions." In other words, the testing system/apparatus should be subjected to the conditions typically found in the oil reservoir from which the core sample was extracted (e.g., elevated temperatures and pressures). The user, therefore, must simulate reservoir conditions by subjecting the core sample to some overburden pressure and by maintaining the fluids flowing through the core sample at a high pressure and temperature. This is accomplished by maintaining high back pressure on the pore fluid(s) when fluid is flowed through the core sample. Pressures up to 5,000 psi are typical, though they can be as high as 20,000 psi for some reservoirs. The volume of the core sample effluents should be measured at the pressure at which they exit the core sample.

In order to measure the effluent volumes of the two (or more) liquids, fluid separators are used. For example, gravity separators made by a number of companies (e.g., Core Laboratories N.V., Vindum Engineering, Inc., and CoreTest Systems, Inc.) may be used to separate the fluid effluent. In one embodiment, the fluid separators may also include an acoustic transducer and associated electronics in order to provide feedback control in determining relative permeability (described in greater detail below).

Generally, fluid separators include two chambers 102, 104 (FIG. 1) or tubes capable of containing high pressure fluids in a high temperature environment. The chambers 102, 104 are fluidly interconnected at both an upper portion 114 and a lower portion 116 so that the fluid level in one will be the same as the fluid level in the other. Since the fluids are generally immiscible and generally have different densities, the fluids separate, due to gravitational forces, with the less dense, lighter fluid rising to and accumulating in the upper portion 114 of the chambers 102, 104 and the denser, heavier fluid settling to and accumulating in the lower portion 116 of the chambers 102, 104. The fluids in the second chamber 104, referred to as the sensing chamber 104, have a meniscus that forms at the interface between the two fluids (the meniscus is generally present in the first chamber 102 as well, but the meniscus in the second, sensing chamber 104 may be clearer and/or more well defined). An acoustic or ultrasonic transducer 128 is mounted in the base of the second chamber 104. The transducer transmits a pulse which is reflected first off a target 132 at known distance above the transducer 128. The acoustic pulse also reflects off of the meniscus between the two fluids. The time it takes for the pulse to travel to and back from the target is used to calculate the sonic velocity in the denser fluid, thereby enabling a user (e.g., a controller) to calculate the distance to the meniscus, enabling the user to determine the volume of the denser fluid in the second tube 104. Knowing the total volume of the second tube 104 allows one to also know the volume of the lighter fluid in the second tube 104. Once again, as mentioned above, conventional core sample testing systems were difficult to implement because the testing equipment had some finite volume, thereby making it difficult to efficiently and conveniently determine relative permeability. In these types of measurements, permeability of a core sample is determined through pressure drop and flow rate across the sample, given an array of saturation states.

While numerous details, examples, and embodiments herein are directed towards determining relative permeability and/or testing core samples, the subject matter of the present disclosure may be utilized in other industries and to improve other analysis procedures. In other words, the subject matter of the present disclosure can be incorporated into various procedures/analyses that involve measuring volumes of two (or more) immiscible fluids. For example, the subject matter of the present disclosure may be utilized to determine the saturation state of a sample in an electrical resistivity test procedure, or the like.

Figure 1:
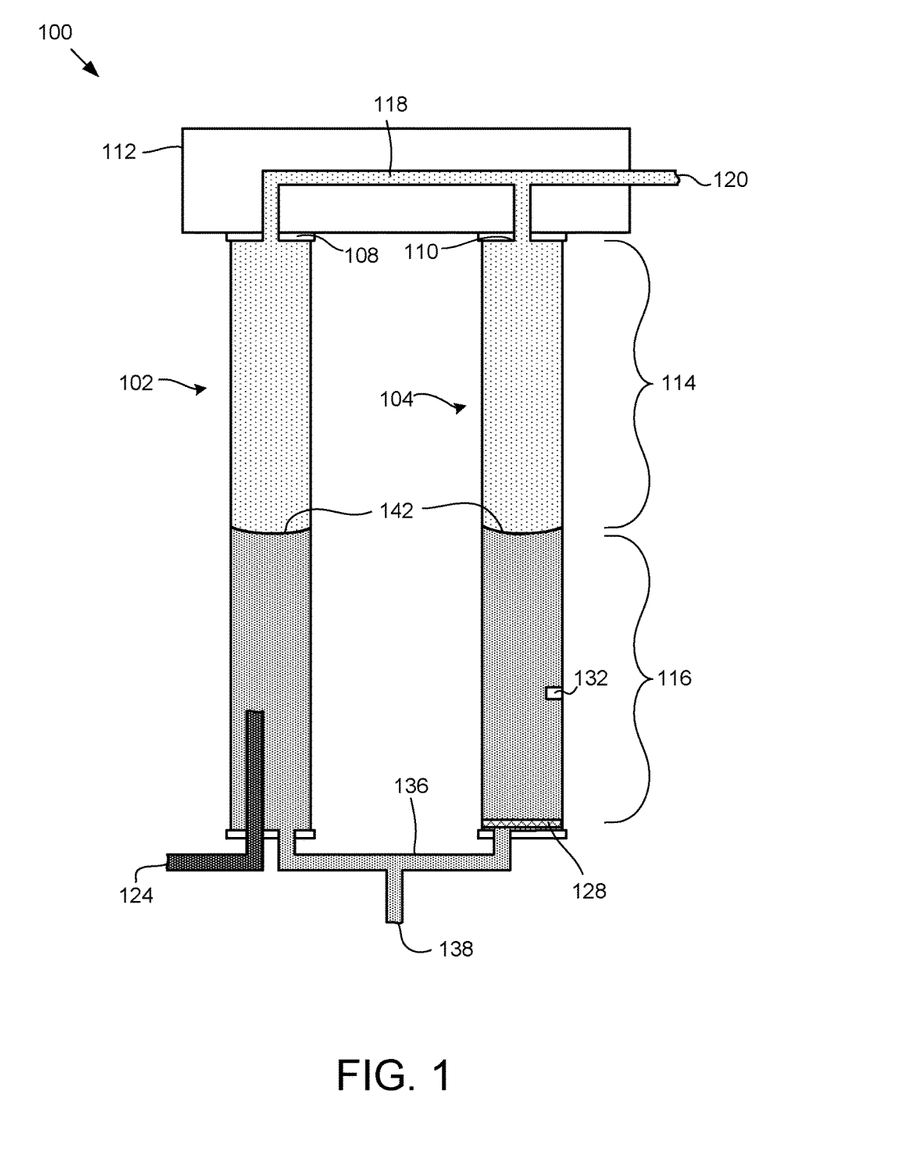
FIG. 1 is a schematic depiction of one embodiment of a two-phase separator.

FIG. 1 is a schematic view of a two-phase separator 100 according to the present disclosure. The separator 100 comprises two measurement tubes, a separator tube 102 and sensing tube 104, vertically mounted and parallel to each other. While two chambers/tubes are shown throughout the figures and pages of the application, it is expected that a single separation chamber may be implemented. In other words, while the dual chamber/tube may perhaps work better in certain situations (e.g., because the meniscus in the sensing tube 104 may be clearer and/or better defined because there are no disturbances caused by direct inlet fluid flow), a single separation chamber may be used to perform the analysis described herein.

According to one embodiment, the tubes 102, 104 each have a precision bore, with a fine internal surface finish, and may be coated with a coating which encourages the formation of a uniform meniscus between two immiscible fluids, as described further below. The tube materials and wall thicknesses are chosen to suitably contain the fluids at high pressure and high temperature. As mentioned above, the portion of the tubes 102, 104 above the meniscus is referred to as the upper portion 114 and the portion of the tubes 102, 104 below the meniscus is referred to as the lower portion 116. In one embodiment, the separator tube 102 has an end cap 108 and the sensing tube 104 has a similar end cap 110. The end caps 108 and 110 are connected to an upper connection block 112 via connection tubes. The upper connection block 112 may be useful for mounting the apparatus. A lower-density fluid connection passage 118 disposed in the upper connection block 112 enables fluid communication between the tubes 102, 104. The upper block 112 also contains an outlet port 120 for the lower-density, lighter fluid.

In one embodiment, the measurement tubes 102, 104 are mounted into a base block that also facilitates mounting. An inlet port 124 is disposed in the base block is connectable in fluid receiving communication with a core sample holder to receive effluent from the core sample. The inlet port directs flow to the separator tube 102. The inlet port may extend into the separator tube 102 a certain distance (e.g., may extend partially up through the separator tube 102) to prevent any of the lighter fluid from inadvertently passing into the lower connection passage 136.

The apparatus 100 includes a meniscus position detector. In one embodiment, as described above, the meniscus position detector includes an acoustic transducer 128 in fluid contact with the heavier fluid in the sensing tube 104. An acoustic target 132 may be disposed in the sensing tube 104 and an electrical connector connects the transducer 128 to the system electronics (not shown). In other embodiments, the meniscus position detector includes is an optical position sensor or some other mechanism for determining the position/height of the meniscus in the sensing tube 104. A lower fluid connection passage 136 provides fluid communication between the tubes and a lower outlet port 138 is fluidly connected to the connection passage 136.

Figure 2:
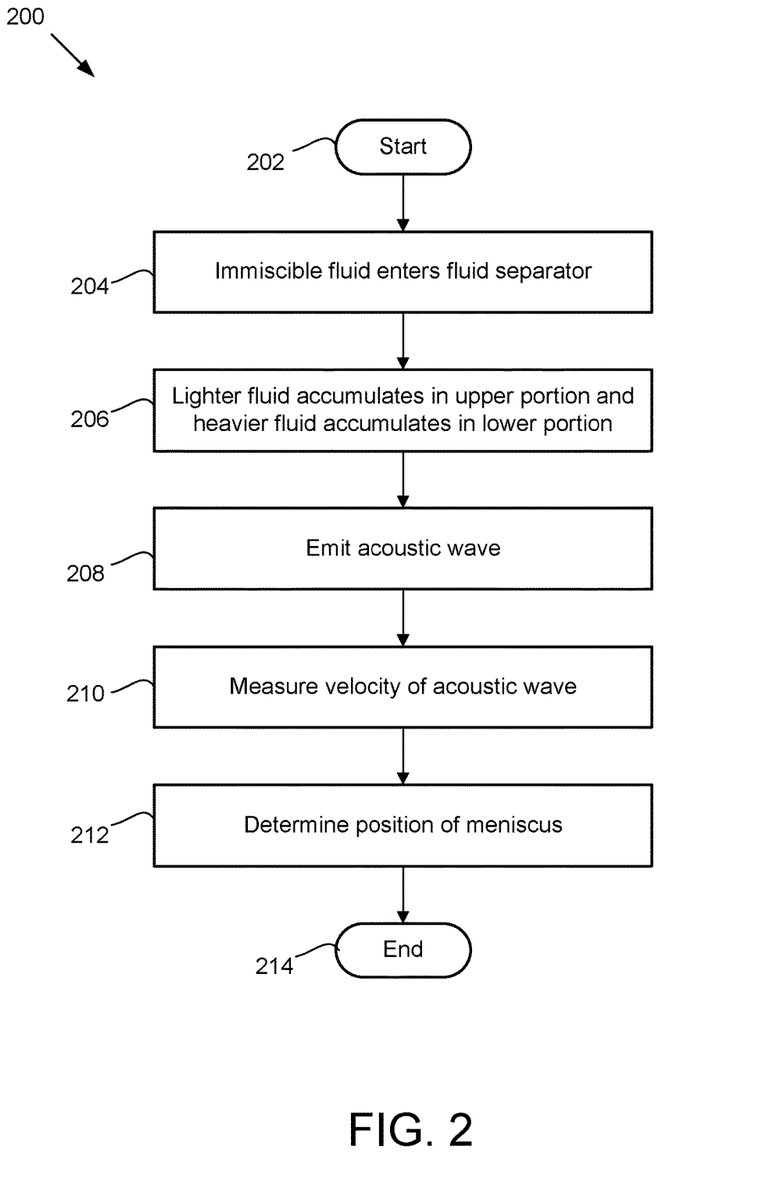
FIG. 2 is a schematic flow-chart diagram illustrating one embodiment of a method of using the two-phase separator of FIG. 1.

FIG. 2 is a schematic flow chart diagram illustrating one embodiment of a method 200 of using the separator of FIG. 1, or similar apparatuses, according to the present disclosure. The method 200 begins at step 202, and at step 204 a two-phase fluid enters the separation tube 102 through inlet port 124. In one embodiment, the fluid is brine mixed with oil, though other fluids and mixtures of fluids may be used. For example, carbon dioxide may also or alternatively be used. At step 206, gravitational forces cause the lower density fluid—oil—to rise and the higher-density fluid—brine—to fall, thereby separating the fluids within the separator tube 102. The fluids, whether or not completely separated from each other, enter the sensing tube 104 via the connection pathways 118, 136. The lighter fluid flows through the upper connection pathway 118, and heavier fluid flows through the lower connection pathway 136. Because fluid communication between the two tubes 102, 104 is restricted to the top and bottom of the respective tubes, a well-defined meniscus 142 forms between the two fluids at the same height (i.e., position) in each tube 102 and 104. Because flow from the separation tube 102 to the sensing tube 104 is limited to the passages in the upper block 112 and base block, there is negligible fluid flow and mixing in the vicinity of the meniscus 142 in the sensing tube 104, allowing the meniscus 142 to be stable and undisturbed.

With the meniscus 142 thus providing a suitable reflection surface for acoustic waves, the method 200 includes generating and emitting an acoustic wave that propagates through the higher density fluid in the sensing tube 104. The target 132, mounted a fixed distance from the transducer 128, generates a reflected wave, which is sensed by the transducer 128. The time of the reflection from the target 132 is then used in step 210 to determine the velocity of the acoustic wave through the heavier fluid (in practice, the time of the target reflection is averaged over many cycles to produce a stable and accurate measurement of velocity). In step 212, the meniscus 142 also reflects the acoustic wave generated by the transducer 128 back to the transducer 128, and the distance of the meniscus 142 is then calculated from the time taken to reflect the acoustic wave back to the transducer 128 from the meniscus 142 and the velocity of the wave through the heavier fluid, determined in step 210. The volume of the heavier fluid in the sensing tube 104 can then be determined, since the dimensions of the tube 104 are also known. As mentioned above, it is expected that other mechanism may be employed to detect the position of the meniscus.

The electronics that process the signal generated by the transducer 128 from the reflected acoustic wave off the meniscus 142 detect the impulse in the signal, rather than using wave-form matching techniques. This provides for accurate measurement of the meniscus position at distances very close to the upper end cap 110 of the sensing tube 104. Wave-form matching techniques require more separation between waves reflected off the end cap 110 and waves reflected off the meniscus 142 in order to obtain a clean wave form to evaluate. The current disclosure also incorporates into the signal processing electronics the ability to generate an analog output signal proportional to the position of the meniscus 142, which can be used in embodiments of the disclosure described below. The method 200 ends at 214.

Figure 3:
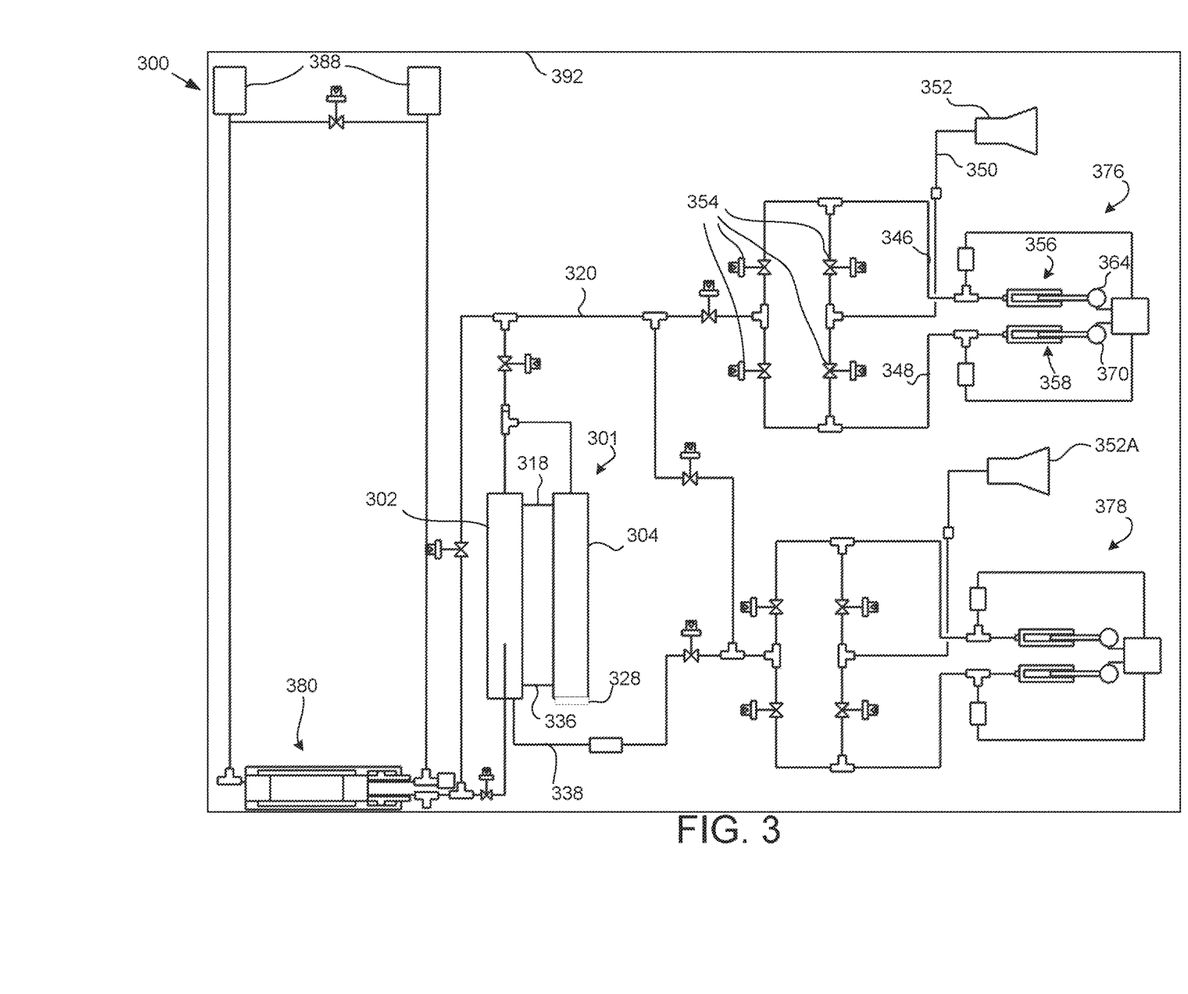
FIG. 3 is a schematic depiction of one embodiment of a multi-phase core flood system.

FIG. 3 is a schematic view illustrating one embodiment of a multi-phase core flood apparatus and system 300, in accordance with the present disclosure, that removes the volume limitation of conventional apparatuses and systems. The apparatus 300 is a back-pressure control, fluid-separation, and fluid volume-measurement system that overcomes volume limitations of the separator 100 alone, provides back pressure control to the flow system, and provides accurate measurement of the two fluid volumes.

The apparatus 300 comprises a two-phase separator 301, which may be the separator 100 or another apparatus which accomplishes the same separation. Generally such separators comprise two measurement tubes with a fluid passage at or near the top (for lighter-density fluid communication between the two measurement tubes) and a fluid passage at or near the bottom (for heavier-density fluid communication), with the first tube being a separator tube and the second tube being a sensing tube. Separator 301 comprises a separator tube 302, a sensing tube 304, an upper connector 318 disposed at the upper ends of the tubes 302 and 304 and providing for fluid communication of the lighter fluid between the two tubes and a lower connector 336 disposed at the lower ends of the tubes 302 and 304 for the heavier fluid. An acoustic transducer 328 is disposed at the bottom of the sensing tube 304, with an electrical connection leading from the acoustic transducer 328. An upper outlet 320 leads from the top of the separation tube 302, and a lower outlet 338 leads from the bottom of the separation tube 302.

Fluidly connected to the upper and lower portions of the fluid separator 301 are two volume pressure actuators ("VPA"s). A first volume pressure actuator 376 fluidly connects to the upper portion outlet of the upper portion of the fluid separator and a second volume pressure actuator 378 fluidly connects to the lower portion outlet of the lower portion of the fluid separator. The first and second volume pressure actuator each has a fluid volume encoder that is configured to determine a net volumetric flow of fluid from the fluid separator 301. In other words, the respective encoders not only keep track of the direction of fluid flow (i.e., whether the fluid is flowing from the fluid separator or into the fluid separator) but also the volume of fluid that is flowing. In addition to monitoring net flow of fluid, the first and second volume pressure actuators are configured to collectively maintain constant back pressure on the fluid separator and maintain the meniscus between the two immiscible fluids in the fluid separator at a constant position. Additional details relating to the first and second volume pressure actuators are included below.

In one embodiment, the volume pressure actuators 376, 378 are pulseless pumps (e.g., syringe pumps). In one implementation, each volume pressure actuator includes two syringe pumps that alternate activity to provide constant, pulseless fluid flow/backpressure. In one embodiment, a pressure sensor is connected to the upper outlet 320, and the upper outlet 320 conducts fluid through a valve configuration 354. The valves of the valve configuration 354, which are controlled by a controller, govern and control the flow of fluid to and from the fluid separator 301 (as described below in greater detail).

An upper fluid passage 346 fluidly connects a syringe pump 356, and the upper fluid passage 348 fluidly connects to a syringe pump 358. The syringe pump 356 comprises a cylinder and a piston (described below in greater detail with reference to FIG. 5), whose position in the cylinder is determined by a servomotor 364 driving a ball-screw drive (not shown) or similar system. The syringe pump 358 similarly comprises a cylinder, a piston, and servomotor 370. A controller 372 controls the motors 364 and 370, which in turn determine the positions of the pistons, respectively. The controller 372 also controls the positions of the valves 354, allowing the controller 372 to determine whether the cylinders, or one of them, are connected to or isolated from the system process, and whether they, or one of them, are connected to the reservoir 352. The controller 372 acts according to signals received from a pressure sensor, as well as the state of fullness of the cylinders, as further described below. Collectively, the syringe pumps 356 and 358, and their associated components and circuitry, make up an upper volume pressure actuator, or VPA, 376. In one embodiment, the upper VPA 376 is controlled in a pressure feedback mode, wherein the controller 372 causes the piston in one of the cylinders to maintain the desired fluid backpressure, as sensed by the sensor, that piston thereby becoming the active piston, and its respective cylinder becoming the active cylinder, being connected to the system process—that is, the upper outlet 320. When the active piston reaches the end of its stroke, whether at the top or bottom of the active cylinder, the controller 372 causes the valves 354 to be repositioned to isolate that piston and cylinder from the upper outlet 320 and connect it to the reservoir 352 in order to refill the cylinder (in the case of the piston being at the bottom of the cylinder) or empty it (in the case of the piston being at the top of the cylinder). At the same time, the controller connects the other piston and cylinder to the upper outlet 320, making that piston and cylinder active. A precision encoder (not shown) monitors the position of the pistons, thus monitoring the volume of fluid received into and/or pumped out of the cylinders.

The upper VPA 376 deals with the less-dense fluid coming from or going into the separator 301, whichever is needed to maintain a given pressure—"upper" is used for convenience based on the less-dense fluid coming from the separator 301; there is no requirement for the upper VPA to be physically positioned at any particular height). A lower volume pressure actuator, or VPA, 378, of similar construction and configuration to the upper VPA 376, deals with the more-dense fluid coming from or going into the separator 301 through the lower outlet 338. The mechanics of fluid distribution and flow are similar in the upper and lower VPAs 376 and 378; the primary difference between them lies in their control. The upper VPA 376 operates in pressure feedback mode, providing back pressure control to the system. The lower VPA 378, in contrast, operates in external feedback control mode, that is, based on the output signal of the acoustic transducer 328. Rather than keep the back pressure at a given level, which is the role of the upper VPA 376, the lower VPA 378 operates to maintain the meniscus between the two fluids in the sensing tube 304 at a constant level. A controller 372A in volume pressure actuator 378 communicates with the acoustic transducer 328 via the electrical pathway to accomplish this task, the controller 372A receiving a signal from the acoustic transducer 328 and controlling the pistons and valves of the lower VPA 378 to maintain the level of the meniscus.

In short, the controller 372 receives a signal from the pressure sensor and controls the pistons and valves of the upper VPA 376 to maintain a constant back pressure, while the controller 372A receives a signal from the acoustic transducer 328 and controls the pistons and valves of the lower VPA 378 to maintain the meniscus at a constant level/position. The upper VPA 376 measures the volume of the less-dense fluid produced, as described above, and the lower VPA 378 similarly measures the volume of the more-dense fluid produced. Because the VPAs 376 and 378 have dual cylinders, they can receive infinite volumes of either fluid, as each VPA can alternately receive fluid in one of its cylinders while dumping the fluid from the other cylinder. Similarly, should a particular fluid be produced in insufficient amounts to maintain back pressure (in the case of the upper VPA 376) or keep the meniscus at a given position (in the case of the lower VPA 378), the VPAs can also deliver fluid from the reservoirs 352 and 352A, measuring the total volume of fluid delivered and/or received via high-resolution encoders.

The apparatus 300 also comprises a core sample holder 380, a less-dense fluid delivery mechanism, and a more-dense fluid delivery mechanism. The fluid delivery mechanisms are the source (or may be in fluid contact with a source) of the fluids. The fluid delivery mechanisms, according to one embodiment, deliver the fluids directly to core sample 380. In another embodiment, the fluid delivery mechanisms deliver their respective fluids to a mixer that mixes the fluids before delivering them to the core sample 380 (which may be held in a core sample holder). Pressure sensors 388 measure the differential pressure across the core sample, a temperature sensor 390 measures the temperature of the incoming fluid(s), and an oven 392 maintains portions of the apparatus 300 at a certain temperature and pressure, as shown. In some embodiments, the oven 392 may encompass more or fewer components of the apparatus 300.

Figure 4:
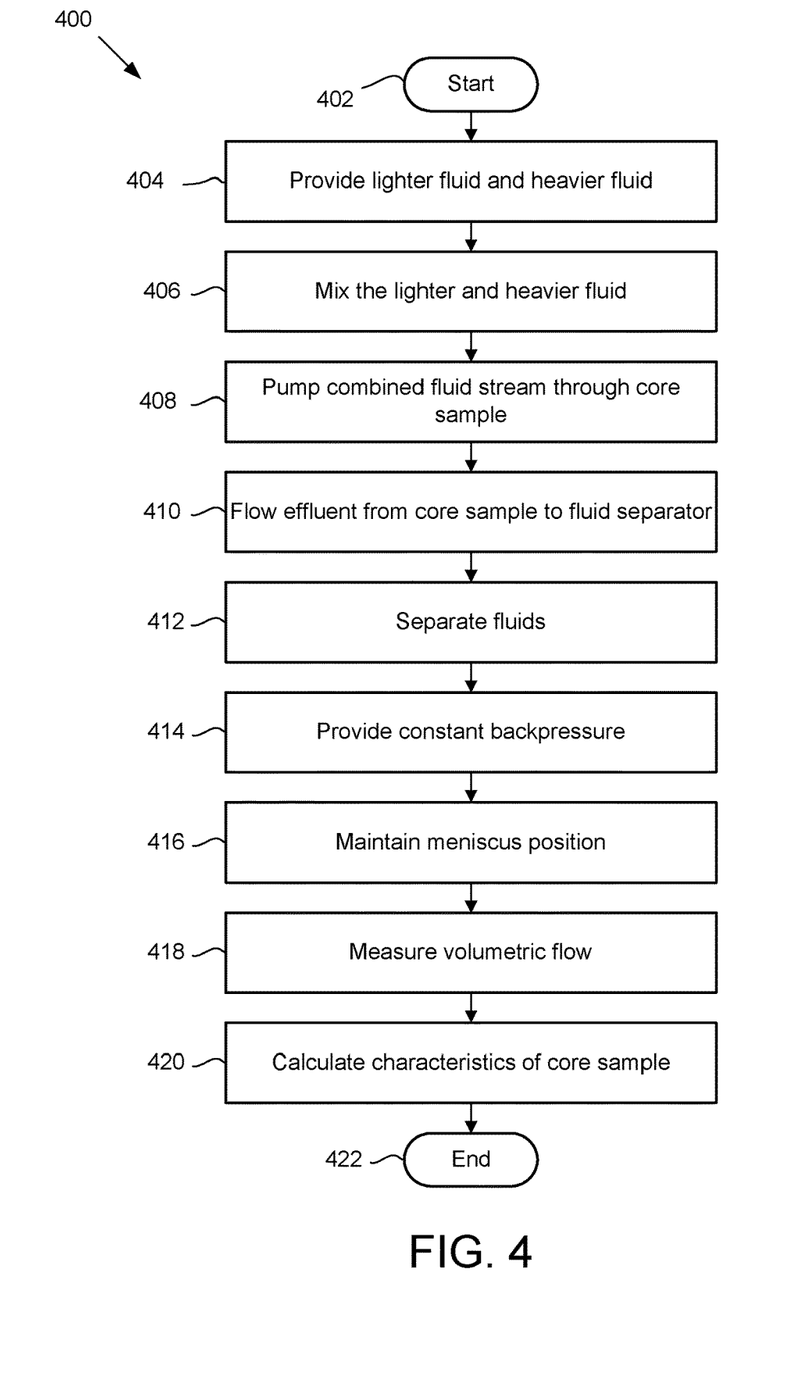
FIG. 4 is a schematic flow-chart diagram illustrating one embodiment of a method of using the core flood system of FIG. 3.

FIG. 4 is a schematic flow-chart diagram illustrating one embodiment of a method of using the core flood system of FIG. 3 in accordance with the present disclosure. The method of FIG. 4 starts at 402, and in step 404 the fluid delivery mechanisms deliver their respective fluids at a given proportion, be it 100% less-dense, 100% more-dense fluid, 50% from each, or some other percentage. The fluid delivery mechanisms, along with their associated circuitry, components, reservoirs, servomotors, fluid passages, and so forth, may operate similarly to the operation of VPA 376, described above, except that their sole role is to deliver fluids at a given proportion and pressure, by signal processing and other means apparent to those skilled in the art in light of this disclosure.

Unless the delivery is entirely one fluid or the other, in step 406 the fluids are combined and mixed in the inline mixer 386, and in step 408 are delivered under pressure to the core sample held in the core sample holder 380. The fluid delivery mechanisms pressurize the system, with the VPA 376 providing back pressure, as described above.

In step 410 the core sample effluent is delivered to the separator 301. In step 412 the separator 301 separates the fluids as described above. In step 414, the VPA 376 provides a constant back pressure, delivering and/or receiving less-dense fluid as needed, as described above, and in step 416 the VPA 378 maintains the meniscus at a constant position, delivering and/or receiving more-dense fluid as needed, as described above. In step 418 the volume of fluid delivered and/or received by the VPAs 376 and 378 is measured by high-resolution encoders, as described above, and in step 420 the measured fluid volume is used to calculate the core sample saturation state, as described above and as will be apparent to those skilled in the art in light of this disclosure. The method ends at 422.

Figure 5:
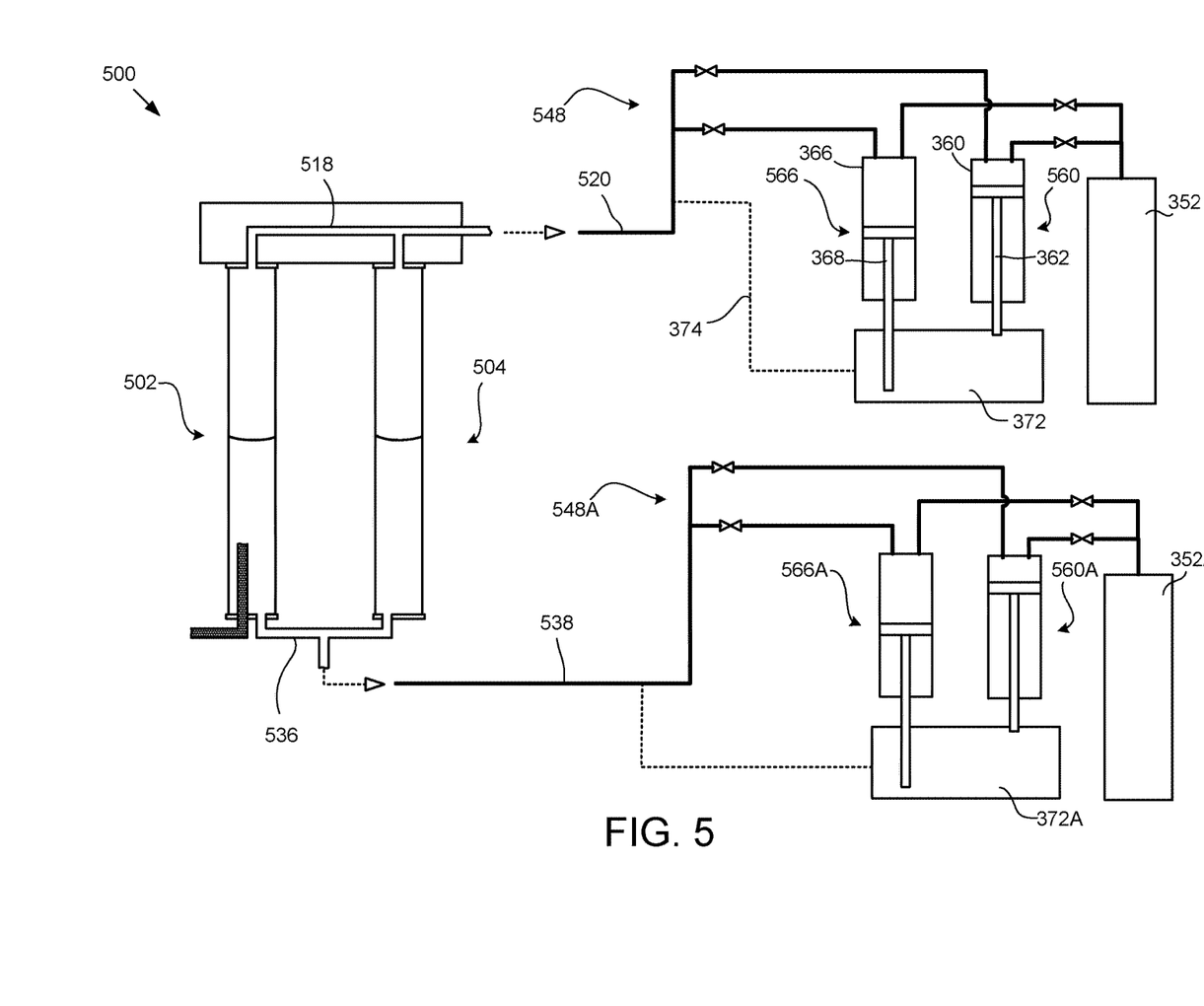
FIG. 5 is a schematic depiction of one embodiment of a continuous flow two-phase separation apparatus.

FIG. 5 is a schematic view illustrating one embodiment of an infinite-flow two-phase separation apparatus 500 according to the present disclosure. The separation apparatus 500 comprises a separator tube 502 and a sensing tube 504, which are operationally connected at or near the tops of the tubes 502 and 504 via an upper fluid connector 518, and at or near the bottoms of the tubes 502 and 504 via a lower fluid connector 536. An upper fluid pathway 520 fluidly connects the upper fluid connector 518 to a manifold or a series of fluid pathways that are controlled by various valves (valve configuration 548) for directing the flow of fluid. Other embodiments within the scope of the disclosure include the upper fluid pathway 520 connecting at or near the top of separator tube 502 or at or near the top of sensing tube 504. The valve configuration 548 fluidly connects to a first upper receptacle 566 and a second upper receptacle 560. As described above, in one embodiment the receptacles are two syringe pumps that work together to generate pulseless backpressure and enable continuous fluid flow. While it is expected that mechanisms other than syringe pumps may be employed to create the pulseless backpressure and continuous flow (e.g., any receptacle that is capable of driving fluid out or receiving fluid in), the term "syringe pump" is nevertheless used throughout the following paragraphs. Accordingly, the present disclosure, although repeated reference is made to syringe pumps, is not limited strictly to syringe pumps.

A lower fluid pathway 538 fluidly connects to the lower fluid connector 536 (or, in other embodiments, at or near the bottom of the separator tube 502 or sensing tube 504) and to valve configuration 548A. The valve configuration 548A fluidly connects to a first lower syringe pump 566A and a second lower syringe pump 560A.

The separation apparatus 500 is configured with valves, sensors, and fluid reservoirs (such as the valve configuration 548, 548A) so that the first and second upper syringe pumps 566 and 560 selectively deliver fluid to or receive fluid from the upper fluid pathway 520, and the first and second lower syringe pumps 566a and 560b selectively deliver fluid to or receive fluid from the lower fluid pathway 538.

The syringe pump 560 comprises a cylinder 360 and a piston 362, whose position in the cylinder 360 is determined by a servomotor 364 (FIG. 3) driving a ball-screw drive (not shown) or similar system. The syringe pump 566 similarly includes a cylinder 366, a piston 368, and servomotor 370 (FIG. 3). A controller 372 controls the motors 364 and 370 (FIG. 3) and thereby controls the position of the pistons 362, 368. The controller 372 also controls the positions of the valves 354, thereby controlling the flow to and from the fluid separator tubes 502, 504. In other words, the controller 372 controls whether the syringe pumps 560, 566, or one of them, are connected to or isolated from the system process, and whether they are connected to the reservoir 352. The controller 372 acts according to signals received from a pressure sensor, as well as the state of fullness of the cylinders 360 and 366, as further described below. Collectively, the syringe pumps 356 and 358, and their associated components and circuitry, constitute the upper volume pressure actuator, or VPA, 376. In one embodiment, the upper VPA 376 is controlled in a pressure feedback mode, wherein the controller 372 causes the piston in one of the cylinders 360, 366 to maintain the desired fluid backpressure, as sensed by the sensor, that piston thereby becoming the active piston, and its respective cylinder becoming the active cylinder, being connected to the system process—that is, the upper outlet 320. When the active piston reaches the end of its stroke, whether at the top or bottom of the active cylinder, the controller 372 causes the valves 354 to be repositioned to isolate that piston and cylinder from the upper outlet 320 and connect it to the reservoir 352 in order to refill the cylinder (in the case of the piston being at the bottom of the cylinder) or empty it (in the case of the piston being at the top of the cylinder). At the same time, the controller connects the other piston and cylinder to the upper outlet 320, making that piston and cylinder active. A precision encoder (not shown) monitors the position of the pistons, thus monitoring and tracking the volume of fluid received into and/or pumped out of the cylinders 360 and 366.

Figure 6:
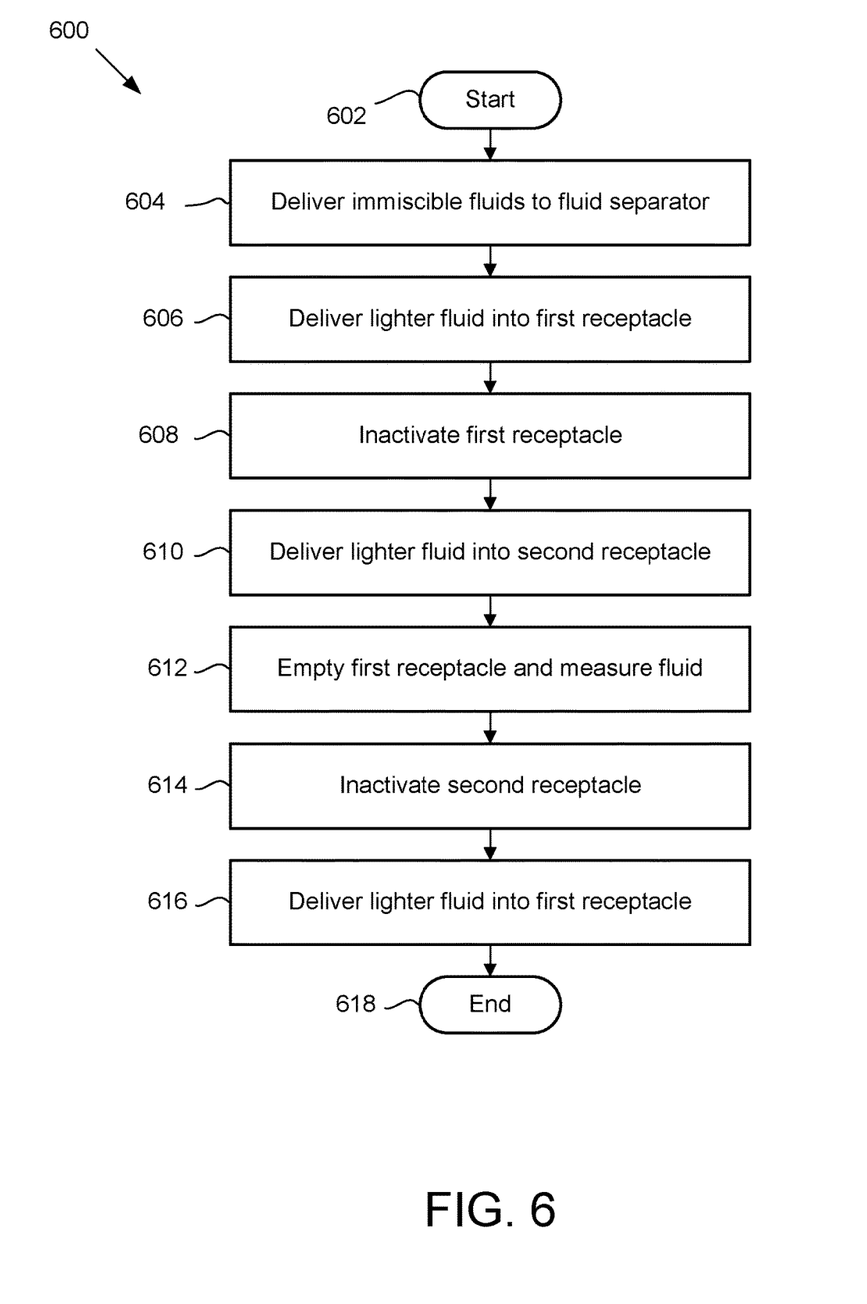
FIG. 6 is a schematic flow-chart diagram illustrating one embodiment of a continuous-flow method.

FIG. 6 is a schematic flow-chart diagram illustrating one embodiment of a method 600 according to the present disclosure, such as by using the separation apparatus of FIG. 5. The method 600 begins at step 602, and at step 604 a two-phase fluid is delivered into a separation system, such as the separator tube 502 and sensing tube 504. At step 606, a less-dense fluid is delivered from the separation system into a first syringe pump, such as the first upper syringe pump 566 via fluid pathways 520. At step 608, when the first syringe pump becomes full, or upon another given condition, the first syringe pump is inactivated. At step 610, the less-dense fluid is delivered into a second syringe pump, such as the second upper syringe pump 560 via fluid pathway 520 and valve configuration 548. At step 612, the less-dense fluid in the first syringe pump is emptied and measured for volume. At step 614, when the second syringe pump becomes full, or upon another given condition, the second syringe pump is inactivated. At step 616, the less-dense fluid is again delivered into the first syringe pump, while the second syringe pump empties and measures its volume of fluid. The method 600 ends at step 618.

The method 600 could be similarly used for delivery of a more-dense fluid into first and second syringe pumps such as first and second lower syringe pumps 566A and 560A, as will be apparent to those skilled in the art in light of this disclosure.

Figure 7:
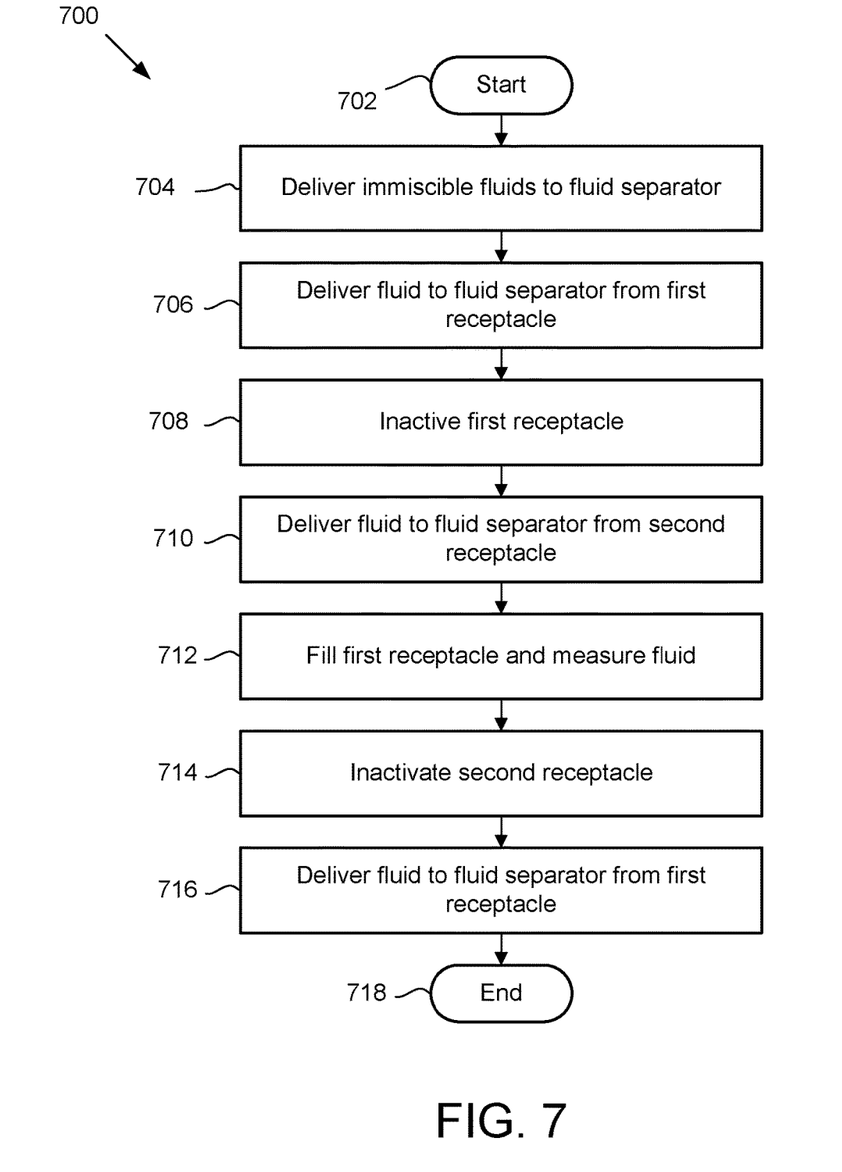
FIG. 7 is a schematic flow-chart diagram illustrating another embodiment of a continuous-flow method.

FIG. 7 is a schematic flow-chart diagram illustrating one embodiment of a method 700 according to the present disclosure, such as by using the separation apparatus of FIG. 5. The method 700 begins at step 702, and at step 704 a two-phase fluid is delivered into a separation system, such as the separator tube 502 and sensing tube 504. At step 706, a less-dense fluid is delivered to the separation system from a first syringe pump, such as the first upper syringe pump 566 via fluid pathways 520. At step 708, when the first syringe pump becomes empty, or upon another given condition, the first syringe pump is inactivated. At step 710, less-dense fluid is delivered into the separation system from a second syringe pump, such as the second upper syringe pump 560 via fluid pathway 520 and valve configuration 548. At step 712, the first syringe pump is filled with less-dense fluid from a reservoir, which fluid is measured for volume. At step 714, when the second syringe pump becomes empty, or upon another given condition, the second syringe pump is inactivated. At step 716, less-dense fluid is again delivered to the separation system from the first syringe pump, while the second syringe pump is filled with less-dense fluid from a reservoir, which fluid is measured for volume. The method 700 ends at step 718.

The method 700 could be similarly used for delivery of a more-dense fluid into the separation system from first and second syringe pumps such as first and second lower syringe pumps 566a and 560a, as will be apparent to those skilled in the art in light of this disclosure.

It will be apparent to those skilled in the art in light of this disclosure that the methods 600 and 700 may be carried out only partially. The methods 600 and 700 may also be combined, including combining only certain steps of each method.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C; or some other suitable combination. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As will be appreciated by one skilled in the art, aspects of the present disclosure may be embodied as a system, method, and/or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency (RF), or the like, or any suitable combination of the foregoing In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present disclosure may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be shared, simultaneously serving multiple customers in a flexible, automated fashion. The computer program product may be standardized, requiring little customization and scalable, providing capacity on demand in a pay-as-you-go model.

The computer program product may be stored on a shared file system accessible from one or more servers. The computer program product may be executed via transactions that contain data and server processing requests that use Central Processor Unit (CPU) units on the accessed server. CPU units may be units of time such as minutes, seconds, hours on the central processor of the server. Additionally the accessed server may make requests of other servers that require CPU units. CPU units are an example that represents but one measurement of use. Other measurements of use include but are not limited to network bandwidth, memory usage, storage usage, packet transfers, complete transactions etc.

Aspects of the embodiments may be described above with reference to schematic flowchart diagrams and/or schematic block diagrams of methods, apparatuses, systems, and computer program products according to embodiments of the disclosure. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present disclosure. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An apparatus for measuring volumes of two or more immiscible fluids, a lighter fluid and a heavier fluid, the apparatus comprising:
   a fluid separator configured to gravity separate the two immiscible fluids, the fluid separator comprising an inlet, an upper portion, an upper portion outlet, a lower portion, and a lower portion outlet, wherein the lighter fluid is configured to accumulate in the upper portion of the fluid separator and the heavier fluid is configured to accumulate in the lower portion of the fluid separator, wherein a meniscus forms between the lighter fluid and the heavier fluid;
   a first volume pressure actuator fluidly connected to the upper portion outlet of the upper portion of the fluid separator, the first volume pressure actuator comprising a first fluid volume encoder configured to determine a net volumetric flow of the lighter fluid from the upper portion of the fluid separator; and
   a second volume pressure actuator fluidly connected to the lower portion outlet of the lower portion of the fluid separator, the second volume pressure actuator comprising a second fluid volume encoder configured to determine a net volumetric flow of the heavier fluid from the lower portion of the fluid separator;
   wherein the first and second volume pressure actuators are configured to collectively maintain constant back pressure on the fluid separator and maintain the meniscus between the two immiscible fluids in the fluid separator at a constant position.

2. The apparatus of claim 1, wherein the fluid separator is a first fluid separator and the apparatus further comprises a second fluid separator and a third volume pressure actuator, wherein the apparatus is configured to determine relative permeability of three immiscible fluids.

3. The apparatus of claim 1, wherein the apparatus is configured to determine relative permeability of "n" number of immiscible fluids, wherein the apparatus comprises "n" number of volume pressure actuators.

4. The apparatus of claim 1, wherein the first volume pressure actuator is configured to maintain the constant back pressure on the fluid separator.

5. The apparatus of claim 1, wherein the second volume pressure actuator is configured to maintain the meniscus between the two immiscible fluids in the fluid separator at a constant position.

6. The apparatus of claim 1, wherein the fluid separator comprises two chambers, wherein the respective upper portions of the two chambers are fluidly interconnected via an upper connector and the respective lower portions of the two chambers are fluidly interconnected via a lower connector.

7. The apparatus of claim 1, wherein each of the first and second volume pressure actuators comprises a pulseless syringe pump unit.

8. The apparatus of claim 7, wherein each pulseless syringe pump unit comprises two syringe pumps.

9. The apparatus of claim 1, wherein the apparatus further comprises a meniscus position detector.

10. The apparatus of claim 9, wherein the meniscus position detector comprises an acoustic transducer.

11. The apparatus of claim 10, wherein the meniscus position detector comprises an optical sensor.

12. An apparatus for measuring volumes of two or more immiscible fluids, a lighter fluid and a heavier fluid, the apparatus comprising:
   a fluid separator configured to gravity separate the two immiscible fluids, the fluid separator comprising a first and a second chamber, wherein the first chamber comprises and inlet, wherein each chamber comprises an upper portion and a lower portion, wherein the upper portion of the chambers are fluidly interconnected via an upper fluid connection passage and the lower portion of the chambers are fluid interconnected via a lower fluid connection passage, wherein the lighter fluid is configured to accumulate in the upper portion of the chambers and the heavier fluid is configured to accumulate in the lower portion of the chambers, wherein a meniscus forms between the lighter fluid and the heavier fluid in the chambers, wherein the interconnected upper portion of the chambers comprises an upper portion outlet and the lower portion of the chambers comprises a lower portion outlet;
   a first volume pressure actuator fluidly connected to the upper portion outlet, the first volume pressure actuator comprising two syringe pumps that each have first fluid volume encoders configured to determine a net volumetric flow of the lighter fluid to and from the upper portion of the chambers of the fluid separator;
   a second volume pressure actuator fluidly connected to the lower portion outlet, the second volume pressure actuator comprising two syringe pumps that each have second fluid volume encoders configured to determine a net volumetric flow of the heavier fluid to and from the lower portion of the chambers of the fluid separator; and
   a meniscus position detector comprising an acoustic transducer;
   wherein the first and second volume pressure actuators are configured to collectively maintain constant back pressure on the fluid separator and maintain the meniscus between the two immiscible fluids in the fluid separator at a constant position.

13. A method for measuring volumes of two or more immiscible fluids, a lighter fluid and a heavier fluid, the method comprising:
- pumping at least one of the lighter fluid and the heavier fluid through the core sample;
- flowing a fluid effluent from the core sample into a fluid separator, wherein the lighter fluid accumulates in an upper portion of the fluid separator and the heavier fluid accumulates in a lower portion of the fluid separator, wherein a meniscus forms between the lighter fluid and the heavier fluid;
- determining net volumetric flow of the lighter fluid from the upper portion of the fluid separator via a first volume pressure actuator that is fluidly connected downstream of the upper portion of the fluid separator;
- determining net volumetric flow of the heavier fluid from the lower portion of the fluid separator via a second volume pressure actuator that is fluidly connected downstream of the lower portion of the fluid separator; and
- maintaining constant back pressure on the fluid separator and maintaining the meniscus at a constant position in the fluid separator via the first and second volume pressure actuators.

14. The method of claim 13, wherein inlet flow of fluid through the core sample consists of the at least one of the lighter fluid and the heavier fluid and outlet flow of fluid from the core sample consists of the fluid effluent.

15. The method of claim 13, wherein at least one of the lighter fluid and the heavier fluid is continuously pumped through the core sample until a steady state condition is achieved.

16. The method of claim 13, wherein the fluid separator comprises two chambers, wherein the respective upper portions of the two chambers are fluidly interconnected via an upper connector and the respective lower portions of the two chambers are fluidly interconnected via a lower connector.

17. The method of claim 13, wherein all of the method steps are performed under temperature and pressure conditions that are representative of the core from which the core sample was extracted.

18. The method of claim 17, wherein the pressure condition under which the method steps are performed is at least 5,000 psi.

19. The method of claim 13, wherein each of the first and second volume pressure actuators comprises a pulseless syringe pump unit.

20. The method of claim 19, wherein each pulseless syringe pump unit comprises two syringe pumps.

* * * * *